United States Patent [19]
Nakamura et al.

[11] Patent Number: 5,812,264
[45] Date of Patent: Sep. 22, 1998

[54] METHOD OF MEASURING SURFACE REFLECTANCE AND A METHOD OF PRODUCING ANTIREFLECTIVE POLARIZING FILM

[75] Inventors: Kimishige Nakamura, Ibaraki; Hiroshi Ishida, Akashi; Akio Ohsaki, Niihama, all of Japan

[73] Assignee: Sumitomo Chemical Company, Limited, Osaka, Japan

[21] Appl. No.: 558,608

[22] Filed: Oct. 31, 1995

[30] Foreign Application Priority Data

Oct. 31, 1994 [JP] Japan ................................ 6-266560
Nov. 4, 1994 [JP] Japan ................................ 6-271315

[51] Int. Cl.$^6$ ................................ G01J 4/00; G01J 3/28
[52] U.S. Cl. ................................ 356/369; 356/327; 250/225
[58] Field of Search ................................ 356/364, 369, 356/327, 429; 250/225

[56] References Cited

U.S. PATENT DOCUMENTS

| | | | |
|---|---|---|---|
| 3,985,447 | 10/1976 | Aspues | 356/369 |
| 4,653,908 | 3/1987 | Yajima et al. | 356/327 |
| 4,850,711 | 7/1989 | Sano et al. | 356/369 |
| 5,333,052 | 7/1994 | Finarov | 356/369 |
| 5,335,066 | 8/1994 | Yamada et al. | 356/369 |

OTHER PUBLICATIONS

Shurcliff, "Polarized Light: Production and Use," Harvard University Press, 1966, pp. 132–139.

Primary Examiner—Frank G. Font
Assistant Examiner—Jason D. Vierra-Eisenberg
Attorney, Agent, or Firm—Cushman Darby & Cushman IP Group of Pillsbury Madison & Sutro, LLP

[57] ABSTRACT

A method of measuring surface reflectance of a polarizing film product and for producing an antireflective polarizing film. The method includes placing a linear polarizer between a polarizing film product and a light supplying part, and measuring light reflected by the surface of the film.

11 Claims, 3 Drawing Sheets

METHOD OF MEASURING SURFACE REFLECTANCE AND A METHOD OF PRODUCING ANTIREFLECTIVE POLARIZING FILM

BACKGROUND OF THE INVENTION

1. Field of the Invention

The present invention relates to a method of measuring surface reflectance of a polarizing film product such as antireflective polarizing films, used for optical components such as liquid crystal displays, and a method of producing an antireflective polarizing film by using the measurement method.

2. Related Prior Art

Recently, liquid crystal displays have been used in the field of television, office automation equipment, etc. and applied widely to video camera monitors, information terminals used inside automobiles, etc. As the field of application is enlarged, requests for antireflection protection against external light are increasing, and polarizing films coated on display surfaces are also required to be antireflective. In the present specification, polarizing films provided with an antireflective property are sometimes referred to as "antireflective polarizing films."

Such antireflective polarizing films are obtained, for example, by forming a single layer or multiple layers of antireflective thin films having low refractive indexes such as those made of magnesium fluoride, silicon dioxide, etc. and/or films having high refractive indexes such as those made of zirconium oxide, tin oxide, indium oxide, titanium oxide, etc., on a polarizing film.

As an example of antireflective film coated with a single layered thin film, the film using magnesium fluoride having a low refractive index, whose optical film thickness (nd) is about a quarter of the wavelength of visible light, is known. The optical film thickness (nd) is a value defined by the product of the refractive index (n) and the film thickness (d).

As an example of antireflective film coated with multi-layered thin film, the film whose multilayered thin film comprises four layers of zirconium oxide, silicon dioxide, titanium oxide and silicon dioxide made by a vacuum evaporation coating method or a sputtering method, is disclosed in Japanese Unexamined Patent Publication (Kokai) No. 62-178901.

Since these antireflective films deliver an antireflection capability by canceling light reflected by each layer through interference, it is necessary to form the thin film so that the optical film thickness of the layer is as close as possible to its predetermined value in order to obtain an antireflective film having superior characteristics. In addition, since the refractive index of the thin film is determined by a material to be used, the optical film thickness is substantially controlled by the thickness of the thin film.

An indirect method is known for monitoring the film thickness of each antireflective thin film layer in an antireflective film forming method such as the vacuum evaporation coating method and the sputtering method. The method comprises the steps of attaching a film component to a quartz oscillator disposed close to an object, determining the thickness of the film component on the oscillator from the change in the resonance frequency of the oscillator, and calculating the thickness of the thin film attached to the object on the basis of the obtained thickness on the oscillator.

In addition, a method is known for adjusting the thickness of a film, which comprises the steps of installing a monitor board close to an object on which film layers are attached, and measuring a change in the reflectance of the board.

Since the film thickness measurement method using a quartz crystal is an indirect method, the method is not suitable for strict control of the film thickness.

Furthermore, the method of measuring the change in the reflectance of the monitor board installed close to an object on which film layers are attached requires an extra facility which consists of the monitor board, and can be applied only in batch manner.

To obtain an antireflective film having superior characteristics, a method of adjusting the thin film thickness so that the reflectance has a predetermined uniform value eventually can be expected to apply instead of a method of strictly controlling the optical film thickness of thin layers constituting the antireflective film. In order to apply this method, the surface reflectance of the film to be obtained must be measured accurately.

On the other hand, in order to accurately measure the surface reflectance of a polarizing film product, light reflection by the back surface of the polarizing film product must be prevented. One method of preventing such light reflection is to coat black paint on the back surface. However, this method requires complicated procedures, makes the tested products dirty by the black paint treating and results in the loss of the products.

SUMMARY OF THE INVENTION

An object of the present invention is to provide a method of measuring surface reflectance of a polarizing film product accurately and easily without making the objects to be measured dirty.

Another object of the present invention is to provide a convenient and efficient method of producing a uniform antireflective polarizing film.

Accordingly, the present invention relates to a method of measuring surface reflectance of a polarizing film product, which comprises:

placing a linear polarizer between a polarizing film product and a light supplying part so that plane of polarization of the polarizer is normal to that of the polarizing film product, supplying light beam from the light supplying part to the surface of the polarizing film product through the polarizer, and receiving light reflected by the surface.

Furthermore, the present invention relates to a method of producing an antireflective polarizing film by using the method of measuring the surface reflectance of a polarizing film product.

These and other objects and effects of the present invention will become apparent from the following description.

Figure 1:
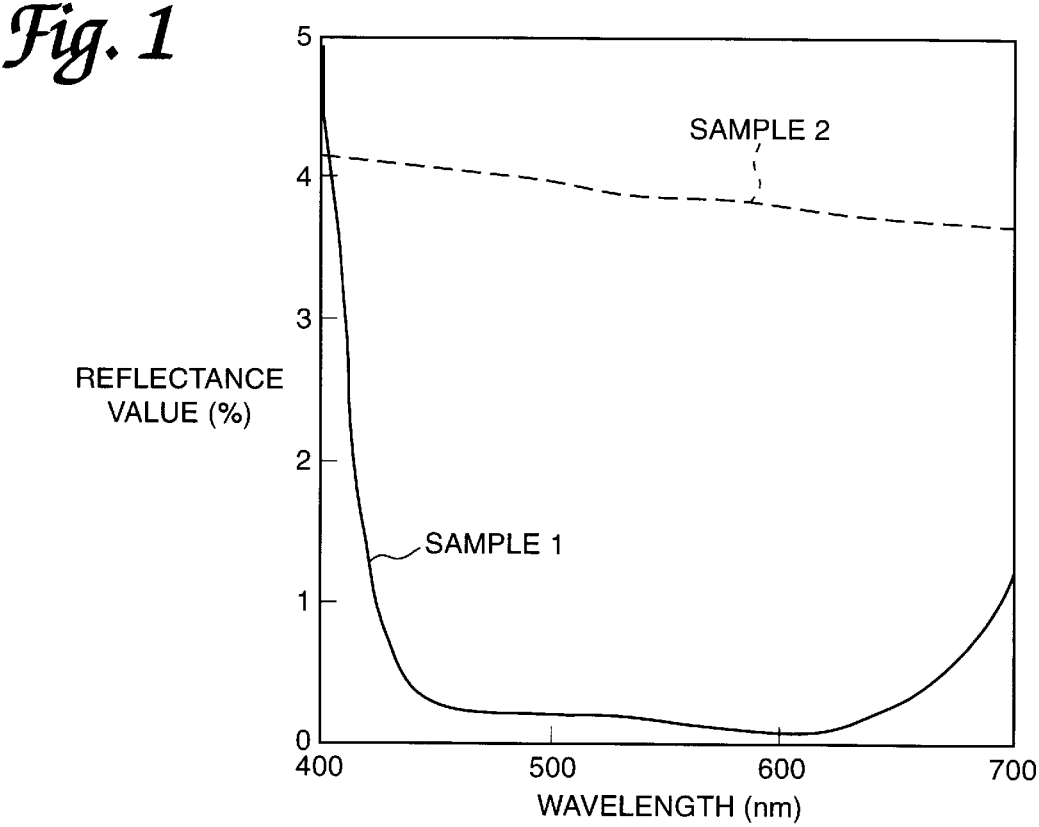
FIG. 1 is a surface reflectance spectrum diagram of Reference Examples 1 and 2.

DESCRIPTION OF REFERENCE CHARACTERS 1, 1': Light supplying and receiving part
2: Polarizing film
3, 3': Polarizer
5: Vacuum container
6: Film delivery unit
7: Film take-up unit
8: Cooling roll
9, 10: Sputtering target cathode assembly
11: First sputtering chamber
12: Second sputtering chamber
13, 14: Reactive gas supply port
15: Partition

DETAILED DESCRIPTION OF THE INVENTION

A Method of Measuring Surface Reflectance of a Polarizing Film Product

Surface reflectance of a polarizing film product can be measured by using a method, which comprises the steps of placing a linear polarizer between a polarizing film product and a light supplying part so that plane of polarization of the polarizer is normal to that of the polarizing film product, supplying light beams from the light supplying part to the surface of the polarizing film through the polarizer, and receiving light reflected by the surface.

The polarizing film product being referred to in the specification is a film wherein a polarizing film is used as a basic material. Examples of such polarizing film product are: an unmodified polarizing film, a polarizing film coated with adhesive, a polarizing film whose surface is subjected to antireflection processing, a polarizing film to which an antireflection-processed film is attached, a polarizing film whose back side surface is laminated with a phase retardation film, a polarizing film mounted on a liquid crystal display, etc.

The polarizer being referred to in the present invention is a so-called linear polarizer used to generate linearly polarized light, which has been described in Chapter 3 "Class and Performance Parameters" of "Polarized Light: Production and Use" written by W. A. Shurcliff, published by HARVARD UNIVERSITY PRESS.

Among those films described above, polarizing films are most conveniently used. In particular, polarizing films subjected to antireflection processing on both sides are superior in practical use.

It is required that the plane of polarization of the linear polarizer is normal to that of a polarizing film product, since this arrangement of the linear polarizer and the polarizing film product is intended so that surface reflectance of the polarizing film product can be measured accurately without being affected by the reflection from the back side of the film product. In other words, the light to the back side of the polarizing film product is shut off by setting the plane of polarization of the linear polarizer normal to that of the polarizing film product. As a result, the effects of the reflection by the back side can be prevented and only the reflection by the top side can be detected.

If the planes of polarization are not normal to each other, the accuracy of measurement drops.

Clearance between the polarizing film product and the linear polarizer is usually about 0 to 5 mm, preferably about 0.1 to 3 mm, more preferably about 1 to 2 mm.

In the case of a long polarizing film product to be measured, by placing a linear polarizer at a predetermined position between the polarizing film product and a light supplying part to have predetermined clearance between the polarizer and the polarizing film product, the surface reflectance of the polarizing film product can be measured continuously in the longitudinal direction while the polarizing film product is run, for example. In other words, the delivery, measurement and take-up of a roll-shaped polarizing film product can be performed as a series of operations.

Clearance between the polarizing film product and the light supplying part is usually about 1 to 10 mm, preferably about 1 to 5 mm, more preferably about 1 to 3 mm.

In the specification, 'light supplying part' means a part which supplies a light beam generated by light source to an object. Form or construction of the part may vary as long as such function can be accomplished. For example, the part includes a light source and light discharging point through which the light beam is supplied to the object. The light discharging point is on an exit of the part. The light beam is transmitted from the light source to the light discharging point usually by a light transmission means, such as an optical fiber.

The measurement of the surface reflectance of the polarizing film product can be performed by supplying a light beam from the light supplying part to the polarizing film product through the polarizer and receiving reflected light in a light receiving part.

In the specification, 'light receiving part' means a part which receives light reflected from the surface of an object and which measures its amount. Form or construction of the part may vary as long as such function can be accomplished. For example, the part includes a photometer and a light receiving point through which the light reaches the photometer. The light receiving point is on a entrance of the part. The light is transmitted from the light receiving point to the photometer usually by a light transmission means, such as an optical fiber.

An apparatus equipped with the light supplying part including a light source having a function to supply a predetermined amount of light beam and with the light receiving part to measure an amount of reflected light is usually used for measurement of surface reflectance.

This kind of apparatus is commercially available, and a SPECTRO MULTI CHANNEL PHOTO DETECTOR (MCPD-1000, made by OTSUKA ELECTRONICS CO., LTD.) can be taken as an example.

Light source is selected appropriately depending on a required light wavelength range. Preferred examples of the light source capable of supplying a predetermined amount of light are a halogen lamp and a xenon lamp.

The photometer used to measure the amount of reflected light which can measure the luminous intensity values in a required wavelength range at one time for each wavelength, is preferable in practical use. Example of the photometer is a photodiode array type photometer.

Clearance between the light receiving part and the polarizing film product is in the same range to the clearance between the above-mentioned light supplying part and the polarizing film product. Usually, the above-mentioned light supplying part is placed close to the light receiving part.

The amount of reflected light is measured by using a method, which comprises the steps of placing the polarizer between the polarizing film product to be measured and the light supplying part, emitting a light beam from the light supplying part to the front surface of the polarizer; that is, supplying the light beam to the surface of the polarizing film product through the linear polarizer; and receiving light reflected by the surface through the linear polarizer. Surface reflectance of the polarizing film product is then calculated.

An example of the surface reflectance measurement method is as follows:

(1) placing a linear polarizer properly with respect to a standard sample having surface reflectance ($R_0$) obtained at a specific wavelength, and measuring luminous intensity of reflected light ($P_1$) in the same wavelength;

(2) removing the standard sample from the above-mentioned setup, measuring in same way by using only the linear polarizer, to obtain luminous intensity of the light reflected by the linear polarizer ($P_2$);

(3) placing a polarizing film product to be measured at the same position as that for the standard sample used in step (1), and measuring in the same way to obtain luminous intensity of the reflected light ($P_3$).

From the values of $P_1$, $P_2$, $P_3$ and $R_0$, surface reflectance of the polarizing film product to be measured (Rs) can be obtained by using [Equation 1] described below.

$$Rs=(P_3-P_2)\div(P_1-P_2)\times R_0 \quad \text{[Equation 1]}$$

When a computer is connected to the above-mentioned apparatus and $P_3$ is measured, the value of the surface reflectance can be obtained instantaneously from the arithmetic operation of the above-mentioned equation by using the values of $P_1$, $P_2$ and $R_0$ which were measured beforehand.

Furthermore, the spectrum of the surface reflectance in a predetermined wavelength range can be obtained by using a method which comprises the steps of 1) placing a spectroscope, such as a prism or a diffraction grating, usually in the light receiving part, especially between the light receiving point and photometer, or in the light supplying part, especially between the light source and the light discharging point; 2) measuring surface reflectance by using the photometer, which can measure the luminous intensity values in the predetermined wavelength range at one time for each wavelength, and 3) using an arithmetic operation means, such as a computer to obtain the spectrum. This method is preferable in practical use. The spectroscope is placed preferably in the light receiving part, especially between the light receiving point and photometer.

Moreover, the distribution of the surface reflectance of a long polarizing film product can be measured by measuring continuously while the polarizing film product is moved, with the light supplying part, the light receiving part and a linear polarizer fixed.

Additionally, with this method, the surface reflectance of a polarizing film product, which cannot be measured easily in usual way, such as a polarizing film attached to a liquid crystal display, can be measured easily.

According to the present invention, the surface reflectance of a polarizing film product can be measured easily and accurately without modifying or damaging the product.

A Method of Producing an Antireflective Polarizing Film

In a method of producing an antireflective polarizing film by forming an antireflective thin film on one side of a polarizing film, the present invention is characterized in that the method comprises the steps of: placing a linear polarizer between a light supplying part and an antireflective thin film formation side of an antireflective polarizing film so that plane of polarization of the linear polarizer is normal to that of the antireflective polarizing film, a supplying light beam from the light supplying part to the surface of the antireflective polarizing film via the polarizer, receiving light reflected by the surface, measuring the surface reflectance of the thin film formation side of the antireflective polarizing film, and finely adjusting the thickness of the antireflective thin film in accordance with the results of the measurement.

Polarizing films which are suitable include, but are not limited to, known and commercially available polarizing films.

Among the polarizing films, those subjected to hard coating are preferable since they are high in surface hardness.

Examples of material which may be used for the antireflective thin film formed on the polarizing film are those having low refractive indexes such as magnesium fluoride, silicon dioxide, etc. and those having high refractive indexes such as zirconium oxide, tin oxide, indium oxide, titanium oxide, etc.. An antireflective polarizing film can be obtained by forming an antireflective thin film constructed from a single layer of one kind thereof or constructed from multiple layers of two or more kinds thereof on the polarizing film.

For forming the antireflective thin film on the surface of the polarizing film, dry-type methods, such as a conventional vacuum evaporation coating method and sputtering method, or wet-type methods can be used.

Among these methods, dry-type methods are most suitable.

In the dry-type methods, antireflective films may be formed in a batch system by putting a single film or a plurality of polarizing films having a predetermined size in a vacuum container wherein thin films are formed. The dry-type methods can also be applied to a continuous system, wherein a roll-type polarizing film is supplied continuously to an element wherein thin films are attached, and the polarizing film is taken up after necessary thin film formation.

Among these, the continuous system is most suitable.

A preset approximate thickness of the antireflective thin film is formed on one side of a polarizing film.

The preset approximate thickness of the antireflective thin film can be determined by an appropriate known method depending on the object and the kind of thin film. A specific example is described in Japanese Unexamined Patent Publication (Kokai) No. 62-178901, etc.

The surface reflectance of the antireflective polarizing film, on one side of which the preset approximate thickness of the antireflective thin film is formed, can be measured by applying the above-mentioned method of measuring surface reflectance of a polarizing film product.

The method is as described above. However, it will be apparent that the measurement is performed by positioning the surface on which the antireflective thin film of the polarizing film is formed so as to face the linear polarizer.

By measuring the surface reflectance and by finely adjusting the thickness of the above-mentioned antireflective thin film in accordance with the measurement results, the target antireflective polarizing film can be obtained.

The fine adjustment described above is defined as an adjustment performed to finely adjust the thickness of the antireflective thin film. This fine adjustment is achieved, for example, by adding a further certain amount of the thin film to the obtained antireflective polarizing film depending on the obtained surface reflectance, by increasing or decreasing the thickness of the thin film deposited to the subsequent polarizing film, or by adjusting the thickness of the thin film to be attached next in the case of a multi-layered thin film. The fine adjustment can be performed by a so-called feedback system.

To increase or decrease the thickness of the thin film, conventional means used to form thin films may be used. The thickness can be changed by increasing or decreasing the generating rate of a film forming component or by increasing or decreasing the retention time of the polarizing film, for example.

According to the present invention, the surface reflectance of the antireflective polarizing film can be measured accurately and easily, and the results of the measurement can be reflected to the adjustment of the formation of antireflective thin films. Therefore, antireflective polarizing films having superior surface reflectance can be produced easily.

EXAMPLES

Although the present invention will be detailed further below in accordance with the examples thereof, the present invention is not limited to the examples.

The measurement methods and materials used for Reference Examples 1, 2, Comparative Examples 1, 2 and Examples 1, 2 are described below.

Measurement of reflectance: The surface reflectance spectrum in a visible light range of 400 to 700 nm was measured by using a reflectance detector (MCPD-1000 made by OTSUKA ELECTRONICS CO., LTD.), which is equipped with light source (halogen lamp) in light supplying part, a photometer (self-scanning type detection element 311C) in light receiving part, which receives light via an optical fiber and a diffraction grating, and a function to calculate obtained values.

* Polarizing film products to be measured:

Sample 1: An antireflective polarizing film, SK1832AP1-HC-AR made by SUMITOMO CHEMICAL CO., LTD., attached to a glass plate Sample 2: A polarizing film, SK1832AP1-HC made by SUMITOMO CHEMICAL CO., LTD., attached to a glass plate

* Linear polarizer: A polarizing film, SK1832A made by SUMITOMO CHEMICAL CO., LTD., subjected to antireflection processing on both sides

* Standard sample: A 250 $\mu$m thick polymethyl methacrylate film coated with a 5 $\mu$m thick hard coat layer on the top side and black paint (paint name: LACQUER No. 540 made by OSAKA YUKI PAINT CO., LTD., thickness: about 100 $\mu$m) on the back side. Surface reflectance values $R_0$ at various wavelengths are: 400 nm; 4.48%, 500 nm; 4.20%, 600 nm; 4.12%, 700 nm; 4.10%).

Reference Examples 1, 2

The reflectance values of samples 1, 2 coated with black paint on their back surfaces (paint name: LACQUER No. 540 made by OSAKA YUKI PAINT CO., LTD., thickness: about 100 $\mu$m) were measured.

FIG. 1 shows the reflectance spectrum of the measurement results.

This is used as the real surface reflectance of each sample.

Comparative Examples 1, 2

Figure 2:
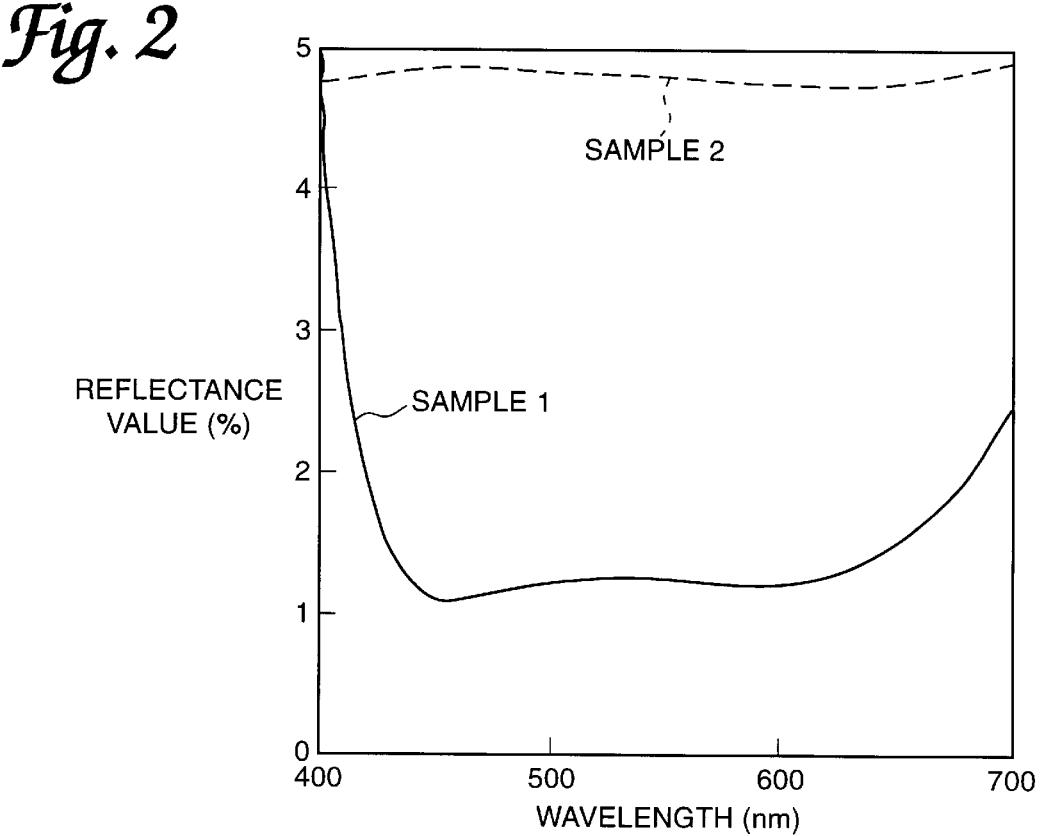
FIG. 2 is a surface reflectance spectrum diagram of Comparative Examples 1 and 2.

The reflectance values of samples 1, 2 were measured with only using the samples. FIG. 2 shows the reflectance spectrum of the measurement results.

The reflectance values are larger by about 1% than those obtained from the results shown in FIG. 1. This increase is caused by the effect of reflection by the back side. It is found that the surface reflectance cannot be obtained accurately by this method.

Examples 1, 2

The intensity of reflected light $P_1$ was measured under the conditions wherein the clearance between the light supplying part of the reflectance measuring instrument and a standard sample was 4 mm, and a polarizer was placed 1 mm away from the standard sample toward the light supplying part.

Next, the standard sample was removed while the above-mentioned positional relations were maintained, and the intensity of light $P_2$ reflected only by the polarizer was measured.

Each of polarizing film product samples 1 and 2 to be measured was placed at the position where the standard sample was placed, and the luminous intensity values $P_3$-1 and $P_3$-2 of light reflected by the samples were measured.

From these values, the surface reflectance values of samples 1 and 2 were obtained in accordance with the above-mentioned [Equation 1].

Figure 3:
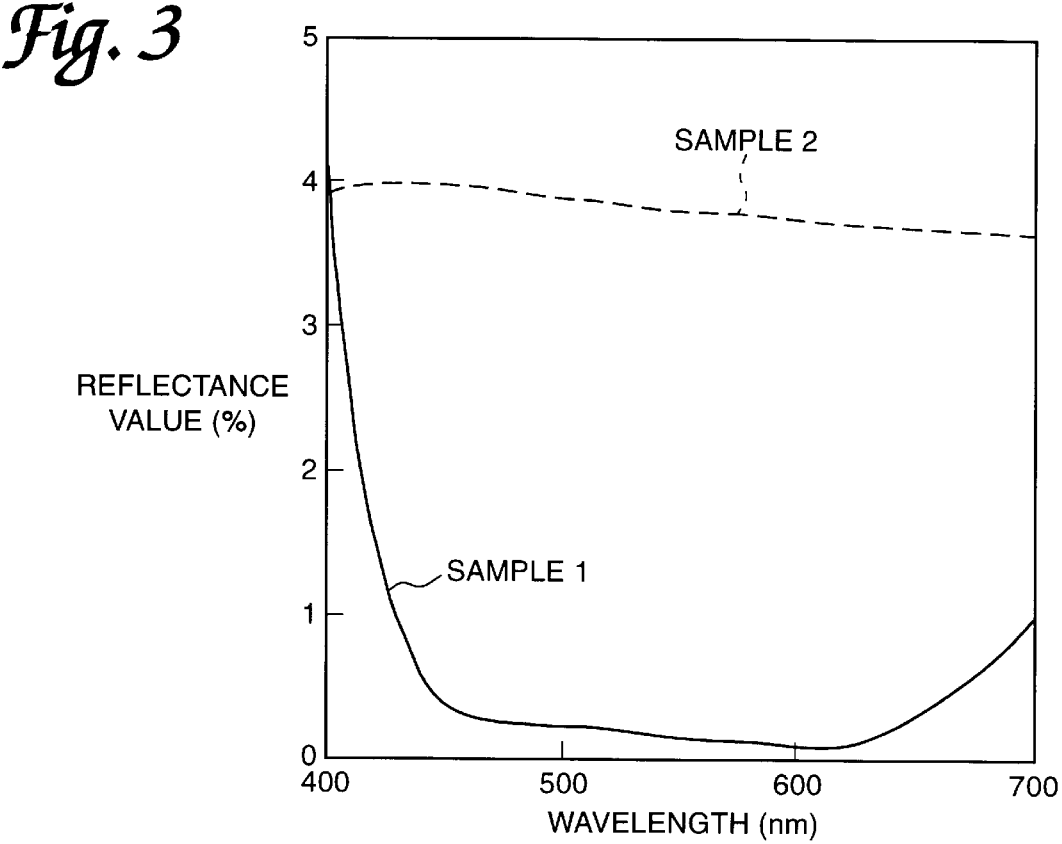
FIG. 3 is a surface reflectance spectrum diagram of Examples 1 and 2.

The results are shown in FIG. 3.

The values of the results coincide well with the surface reflectance values indicated in FIG. 1 for the reference examples 1, 2. It is thus found that the surface reflectance can be measured by this method.

Example 3

Figure 4:
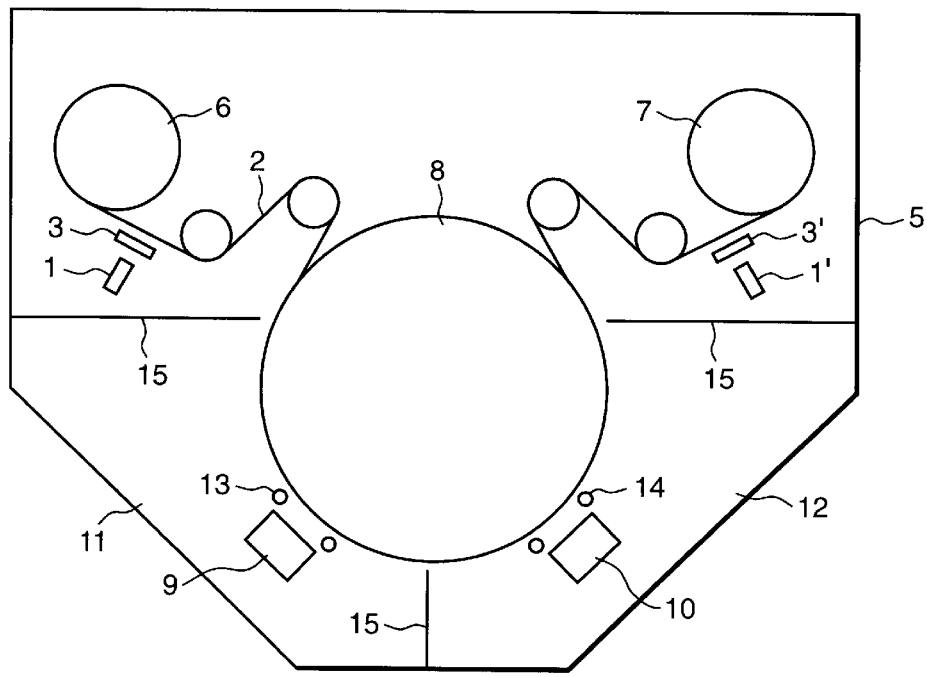
FIG. 4 is a sectional view of a roll coating type sputtering unit of Example 3.

A roll coating type sputtering unit used for this example is shown in FIG. 4.

A polarizing film 2 on which an antireflective thin film to be formed is supplied from a film delivery unit 6 to a first sputtering chamber 11 along a cooling roll 8, and a first layer of thin film is formed in the chamber.

A second layer of thin film is then formed in a second sputtering chamber 12. After forming the second layer of thin film, the surface reflectance of the film is measured by a polarizer 3' and a light supplying and receiving part 1', and the film is taken up by a film take-up unit 7.

Next, the film taken up by the take-up unit 7 is delivered in the reverse direction to the first sputtering chamber 11 along the cooling roll 8 (the second sputtering chamber 11 is simply passed by), and a third layer of thin film is formed in the first sputtering chamber 11. The surface reflectance of the film after the formation of the third layer is measured by a polarizer 3 and a reflectance detector 1 in a similar way, and the film is rewound by the delivery unit 6.

The film is delivered again from the delivery unit 6 to the second sputtering chamber 12 along the cooling roll 8 (the first sputtering chamber 11 is simply passed by), and a fourth layer of thin film is formed in the second sputtering chamber 12. The surface reflectance of the film after the formation of the fourth layer is measured by a combination of the light supplying and receiving part 1' and the polarizer 31, and the film is taken up by the take-up unit 7.

The film is delivered again from the take-up unit 7 to the first sputtering chamber 11 along the cooling roll 8 (the second sputtering chamber 11 is simply passed by), and a fifth layer of thin film is formed in the first sputtering chamber 11. The surface reflectance of the film after the formation of the fifth layer is measured by a combination of the light supplying and receiving part 1 and the polarizer 3, and the film is taken up by the take-up unit 6.

The materials and measurement methods listed below are used.

* Polarizing film: A polarizing film, SK1832A-HC made by SUMITOMO CHEMICAL CO., LTD., subjected to hard coating on the surface

* Polarizer: A polarizing film, SK1832A made by SUMITOMO CHEMICAL CO., LTD., subjected to antireflection processing on both sides

* Standard sample: A 250 μm thick polymethyl methacrylate film coated with a 5 μm thick hard coat layer on the front surface and black paint (paint name: LACQUER No. 540 made by OSAKA YUKI PAINT CO., LTD., thickness: about 100 μm) on the back surface. Surface reflectance values $R_0$ at various wavelengths are: 400 nm; 4.48%, 500 nm; 4.20%, 600 nm; 4.12%, 700 nm; 4.10%).

* Sputtering target: The first sputtering chamber single-crystal silicon (boron-doped), the second sputtering chamber—titanium (purity: 99.9%)

* Sputtering gas: Argon gas

* Reactive gas: Oxygen gas

* Measurement of surface reflectance: a reflectance detector (MCPD-1000 made by OTSUKA ELECTRONICS CO., LTD.), used for Examples 1 and 2, Reference Examples 1 and 2 and Comparative Examples 1 and 2, was also used to measure the surface reflectance spectrum in a visible light range of 400 to 700 nm.

Formation of an antireflective film was started in the conditions indicated below (Table 1).

Figure 5:
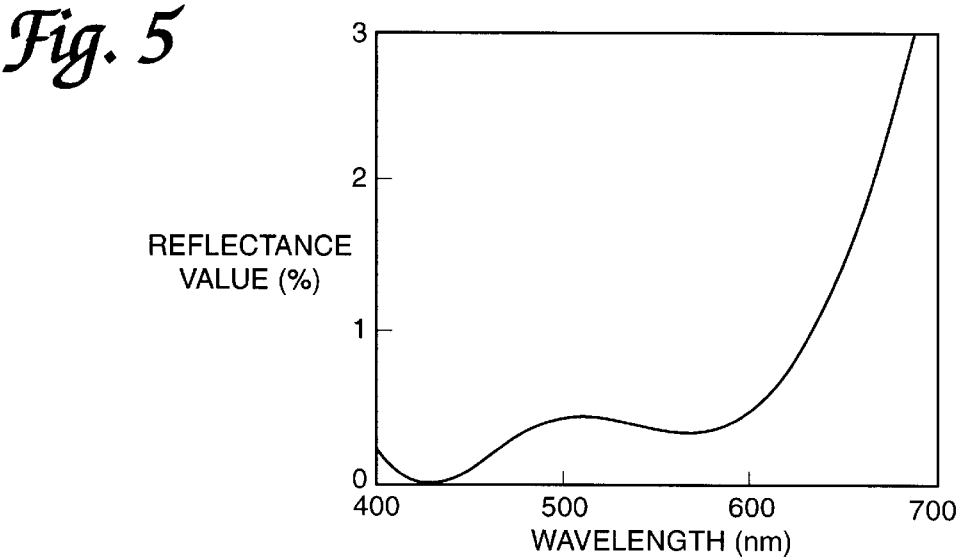
FIG. 5 is a surface reflectance spectrum diagram of an antireflective polarizing film obtained in the initial conditions of Example 3.

FIG. 5 shows the surface reflectance spectrum of the antireflective polarizing film measured by the combination of the light supplying and receiving part 1 and the polarizer 3 after the film formation of the fifth film layer.

However, since this was not the desired spectrum for the antireflective polarizing film, the film speed was changed to 0.22 m/minute while the fifth layer was formed, all other conditions remaining the same.

Figure 6:
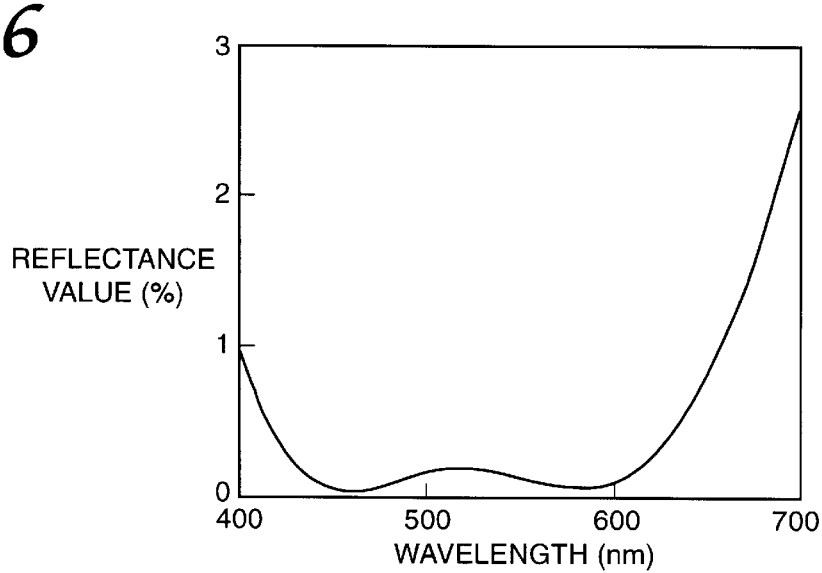
FIG. 6 is a surface reflectance spectrum diagram of an antireflective polarizing film obtained after a first change of conditions of Example 3.

FIG. 6 shows the surface reflectance spectrum measured in the same way after the change of the speed.

Figure 7:
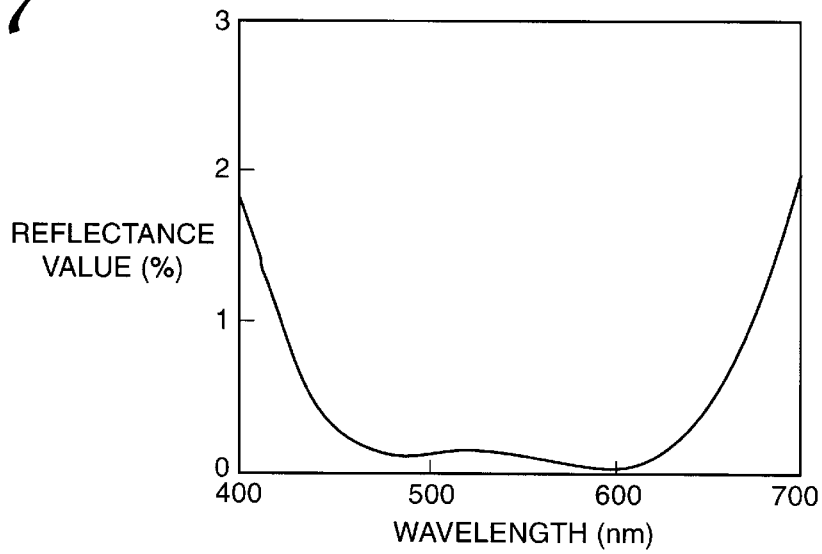
FIG. 7 is a surface reflectance spectrum diagram of the antireflective polarizing film obtained after a second change of conditions of Example 3.

Although this spectrum is acceptable, the surface reflectance in the long wavelength region is still high. The film speed was then changed again to 0.21 m/minute while formation was performed. As a result, an improved surface reflectance spectrum was obtained as shown in FIG. 7.

TABLE 1

| | Thin Film Material | Degree of vacuum (Pa) | Power density (W/cm$^2$) | Film speed (m/min) |
|---|---|---|---|---|
| First layer | Silicon oxide | 0.6 | 10 | 1.4 |
| Second layer | Titanium oxide | 0.6 | 16 | 1.4 |
| Third layer | Silicon oxide | 0.6 | 10 | 0.72 |
| Fourth layer | Titanium oxide | 0.6 | 16 | 0.18 |
| Fifth layer | Silicon oxide | 0.6 | 10 | 0.24 |

We claim:

1. A method of measuring surface reflectance of a polarizing film product, which comprises:

placing a linear polarizer between a polarizing film product and a light supplying part so that plane of polarization of the polarizer is normal to that of the polarizing film product, supplying a light beam from the light supplying part to the surface of the polarizing film product through the polarizer, and receiving light reflected by said surface.

2. The method according to claim 1, wherein the polarizing film product is an unmodified polarizing film, a polarizing film coated with adhesive, a polarizing film whose surface is subjected to antireflection processing, a polarizing film to which an antireflection-processed film is attached, a polarizing film whose back surface is laminated with a phase retardation film or a polarizing film mounted on a liquid crystal display.

3. The method according to claim 1, wherein the linear polarizer is a polarizing film subjected to antireflection processing.

4. The method according to claim 1, wherein the reception of reflected light is performed in a light receiving part.

5. The method according to claim 4, wherein the supply of light beam from the light supplying part and the reception of the reflected light are performed by an apparatus having both light supplying part and light receiving part.

6. The method according to claim 4, wherein the light receiving part comprises a photometer.

7. The method according to claim 6, wherein the light receiving part further comprises a light transmission means.

8. The method according to claim 1, wherein the light supplying part comprises a light source.

9. The method according to claim 8, wherein the light source is a halogen lamp or a xenon lamp.

10. The method according to claim 6, wherein the light supplying part further comprises a light transmission means.

11. The method according to claim 9 or 10, wherein the light receiving part or the light supplying part further comprises a spectroscope.

* * * * *